United States Patent
Eisen et al.

(10) Patent No.: US 7,151,715 B2
(45) Date of Patent: Dec. 19, 2006

(54) METHOD AND APPARATUS FOR DETECTING THE POSITION OF THE EDGE OF A MOVING PRODUCT WEB

(75) Inventors: Juergen Eisen, Augsburg (DE); Wolfgang Krauth, Wulfenshausen (DE); Hang Seibold, Anhausen (DE)

(73) Assignee: Erhardt & Leimer GmbH, Augsburg (DE)

( * ) Notice: Subject to any disclaimer, the term of this patent is extended or adjusted under 35 U.S.C. 154(b) by 118 days.

(21) Appl. No.: 10/917,911

(22) Filed: Aug. 13, 2004

(65) Prior Publication Data

US 2005/0034520 A1   Feb. 17, 2005

(30) Foreign Application Priority Data

Aug. 16, 2003   (DE) ................. 103 37 673

(51) Int. Cl.
    *G01N 29/00* (2006.01)
    *G01N 29/04* (2006.01)
(52) U.S. Cl. ................. 367/129; 73/159; 73/627; 73/629
(58) Field of Classification Search ................. 367/129; 73/159, 627, 628, 629
    See application file for complete search history.

(56) References Cited

U.S. PATENT DOCUMENTS 3,406,887 A    10/1968   Laycak
5,126,946 A *  6/1992    Ko ............................... 73/159
5,565,627 A *  10/1996   Dorr ............................ 73/159
5,834,877 A *  11/1998   Buisker et al. ............. 310/322
6,289,729 B1 * 9/2001    Haque et al. ................. 73/159

FOREIGN PATENT DOCUMENTS

DE    26 54 684       6/1977
DE    34 42 154 C2    8/1989

* cited by examiner

*Primary Examiner*—Ian J. Lobo
(74) *Attorney, Agent, or Firm*—Robert L. Epstein; Epstein Drangel Bazerman & James, LLP

(57) ABSTRACT

A method and an apparatus (1) are used to detect the position of the edge (2) of a moving product web (3). The apparatus (1) has piezoelectric elements (5), which firstly output ultrasonic pulses (10) and secondly pick them up and convert them into an electrical signal. The product web (3) is arranged between the piezoelectric elements (5) and a reflector (11) for this purpose. If the product web (3) is located in the measurement range of the piezoelectric element (5), it attenuates the ultrasonic pulses as a result of reflection or absorption during the double passage of the latter. The position of the product web edge (2) is calculated from this attenuation.

13 Claims, 2 Drawing Sheets

Figure 1:
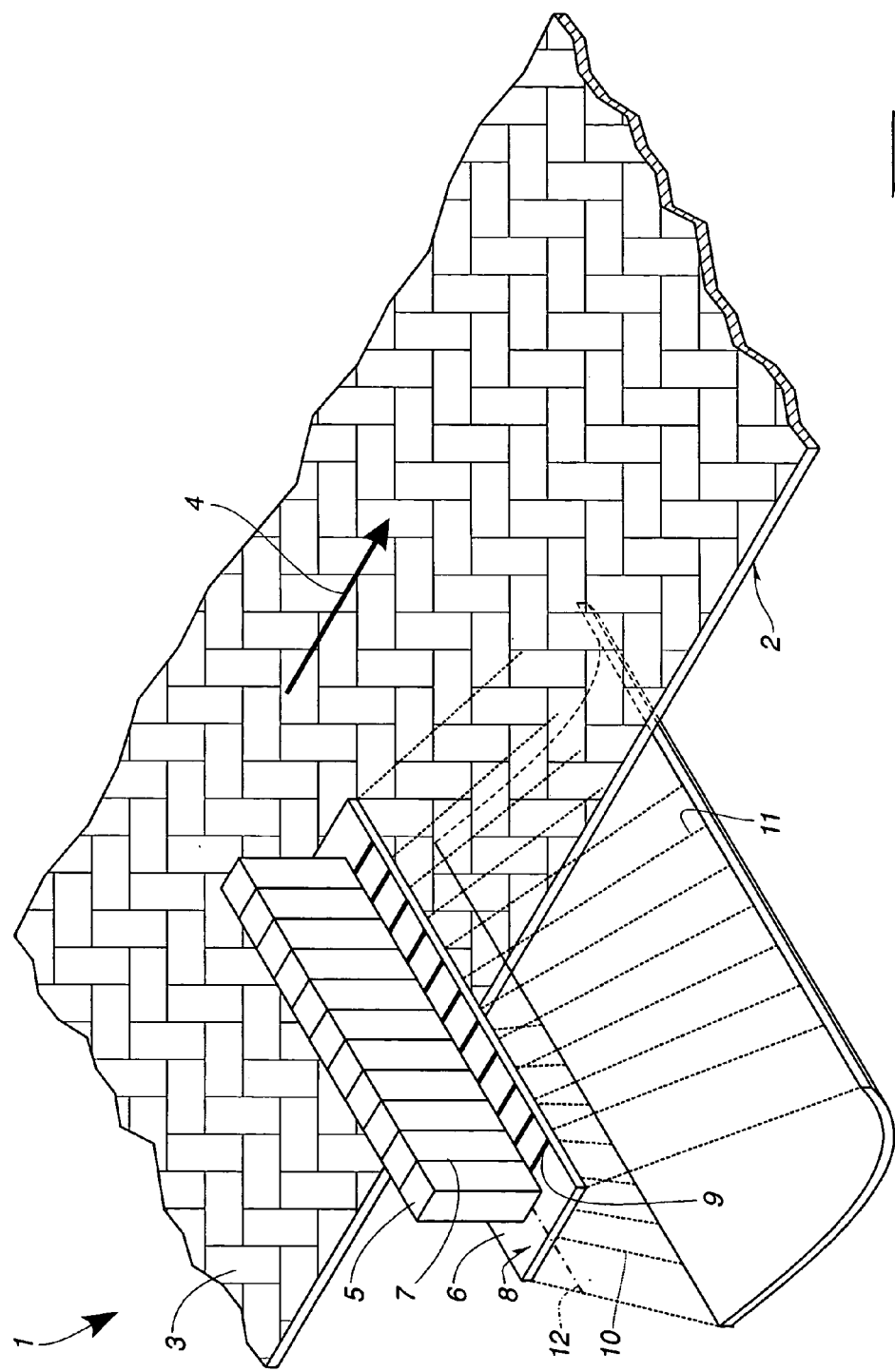

METHOD AND APPARATUS FOR DETECTING THE POSITION OF THE EDGE OF A MOVING PRODUCT WEB

The invention relates to a method for detecting the position of the edge of a moving product web according to the preamble of patent claim 1 and also an apparatus for implementing this method according to the preamble of patent claim 8.

DE 34 42 154 C2 discloses a method for detecting the position of a strip edge of a material web. In this case, an ultrasonic transmitter is aimed at an ultrasonic receiver, the product web being guided between the two. The transmitter supplies ultrasonic pulses which can be detected by the receiver. Here, the time correlation between the output of the ultrasonic pulse and its reception is taken into account when evaluating the received signals. In particular, account is taken only of those received signals which pass from transmitter to receiver on the direct route. In this way, interfering pulses as a result of reflections at the product web or other parts are effectively suppressed. This method has proven to be well worth while in practice and forms the starting point of the present invention.

The invention is based on the object of providing a method and an apparatus for implementing this method of the type mentioned at the beginning which is distinguished by a simple and low-interference construction.

According to the invention, this object is achieved by the features of patent claims 1 and 8.

In the method according to the invention, piezoelectric elements output ultrasonic pulses toward a product web. The product web is in this case preferably non-transmissive, at the most partly transmissive, for the ultrasonic pulses. In this case, it does not matter whether the product web reflects or absorbs the ultrasonic pulses or a combination of the two effects is provided. It is merely important that the ultrasonic pulse energy decreases with increasing coverage of the piezoelectric elements by the product web. As a result of this decrease in the pulse energy, the coverage of the piezoelectric elements and therefore the position of the product web edge can be determined. As a rule, a plurality of piezoelectric elements are arranged beside one another transversely with respect to the web running direction, in order to obtain a sufficiently large measurement range with a high measurement resolution. In order to achieve a simple and simultaneously low-interference construction, the ultrasonic pulses are reflected by a reflector toward the piezoelectric elements which have previously output these ultrasonic pulses. In this case, the product web is arranged between the piezoelectric elements and the reflector, so that the ultrasonic pulses must pass the product web twice. In this way, the transmission coefficient of the product web acts on the ultrasonic pulses with the square of the amplification, so that the dependence of the sonic energy arriving at the piezoelectric elements is correspondingly amplified by the coverage by the product web. In this way, the edge position of the product web can be determined correspondingly more accurately. The piezoelectric elements in this case are used both to output the ultrasonic pulses and to receive the ultrasonic pulses reflected by the reflector and possibly attenuated by the product web. These pulses are converted by the piezoelectric elements into electrical signals, whose amplitude is evaluated in order to determine the product web edge. In this way, the piezoelectric elements are used twice, which means that the expenditure on material and mounting for the sensor arrangement is correspondingly reduced. In addition, transmitter and receiver have the same resonant frequency, which improves the efficiency of the system. Furthermore, the particular advantage results that the transmitting and receiving unit is provided on the same side of the product web. As a result, there is no fork-like construction of the sensor arrangement which, in the event of product web width changes, can possibly lead to destruction of the product web and the sensor elements. Since the reflector is a component which is relatively simple to set up and is inexpensive, if appropriate it can extend over the entire machine width, so that displacement of the reflector in order to adapt to different product web widths can be dispensed with. Therefore, it is merely necessary for the sensor arrangement with the piezoelectric elements to be displaced, which however, as a result of the arrangement provided on one side in relation to the product web, in no way hampers the product web run. The piezoelectric elements are preferably arranged above the product web, so that their active surfaces are aimed downward. In this way, the sensitivity of the sensor arrangement to contamination is low. Since the reflector represents a component which is mechanically very insensitive, it can very easily be kept clean, for example by means of a weak air stream.

In order to achieve a higher measurement resolution transversely with respect to the web running direction, it is important to generate the ultrasonic pulses with little divergence transversely with respect to the web running direction. In order nevertheless to be able to output a sufficiently high pulse energy, it is beneficial to provide a greater divergence of the ultrasonic pulses in the web running direction. In addition, the result is the advantage that the web edge is averaged over a specific length region, so that disruption to the moving product web, such as frayed edges, does not play any part in the detection of the web edge.

Since the piezoelectric elements initially output a high-energy ultrasonic pulse before they are used as receivers, these must be rendered mechanically and electrically quiescent before they can supply usable measured results. For this reason, it is beneficial to begin the evaluation of the electrical signals from the piezoelectric elements only after the expiry of a dead time following the output of the ultrasonic pulse. This ensures that interference with the electrical signals arising from the ultrasonic pulse output previously is reliably avoided.

As a rule, it is not possible to keep the surroundings of the sensor arrangement free of parts which can reflect the ultrasonic pulses. In addition, some of the ultrasonic pulses are also reflected by the product web. These reflected ultrasonic pulses are received by the piezoelectric elements and converted into corresponding electrical signals. In order to avoid these undesired reflections distorting the measured result, it is advantageous if the electrical signals from the piezoelectric elements are evaluated only within a time window. The position of this time window in time in this case depends on the distance of the reflector from the piezoelectric elements, the center of this time window preferably corresponding to twice the signal propagation time between the piezoelectric elements and the reflector. In this way, only the ultrasonic pulses actually reflected by the reflector and getting to the piezoelectric elements without diversion are evaluated, so that interference is kept low.

As a rule, the vertical position of the product web is not absolutely constant. However, a change in the vertical position of the product web can distort the measured result. In particular, it is necessary to take account of the fact that, because of the divergences of the ultrasonic pulses present, their attenuation by a product web dipping partly into the sound cone is all the greater the closer the product web is located to the piezoelectric elements. In order to compensate for this behavior, it is beneficial also to evaluate the time difference between the output of the ultrasonic pulses and an electrical signal from the piezoelectric elements, which signal is generated by a reflection of the ultrasonic pulses by the product web. From this time difference, the distance of the product web from the piezoelectric elements can be determined very simply, in order by using this to correct the calculated coverage of the piezoelectric elements by the product web. In this way, the result is a substantial improvement in the measurement accuracy of the sensor arrangement. In order to achieve a sufficiently strong reflected signal from the product web, the piezoelectric elements are preferably aligned at right angles to the plane of the product web. If this additional evaluation of the reflected signal from the product web is not used, then the piezoelectric elements can also be aligned at an acute angle to the plane of the extent of the product web. In this case, the reflected signal caused by the product web passes the resonator 6 and is therefore not detected.

In order to achieve a sufficiently high sound energy, it is beneficial to generate the ultrasonic pulses simultaneously from a plurality of piezoelectric elements. In order to achieve a sufficiently high local resolution, however, the reflected ultrasonic pulse is evaluated only by a single piezoelectric element, preferably the central piezoelectric element.

In order to achieve as high as possible a level of sound energy arriving at the piezoelectric elements, it is advantageous if the reflector focuses the ultrasonic pulses, at least in the web running direction. In this way, the divergence of the ultrasonic pulses which is present and possibly also desired does not have a detrimental effect on their detectability. Given optimum focusing of the ultrasonic pulses by the reflector, a major part of the ultrasonic energy output is radiated back onto the piezoelectric elements again, so that the result is a correspondingly strong and consequently low-noise electrical signal for the evaluation of the coverage by the product web.

The apparatus according to the invention has proved to be worthwhile for implementing the method. It has piezoelectric elements which output ultrasonic pulses. These are preferably arranged beside one another transversely with respect to the product web running direction, in order to achieve a sufficiently large measurement range for detecting the position of the product web edge. The ultrasonic pulses output by piezoelectric elements are reflected by a reflector, and the reflected sound waves are in turn detected by the piezoelectric elements. The piezoelectric elements are therefore used as a transmitting and receiving unit, so that the entire sensor structure is provided on one side with respect to the product web. Depending on the coverage of the piezoelectric elements, the product web attenuates the ultrasonic pulses, so that the coverage by the product web and therefore the position of the product web edge can be determined by using the sound energy received.

In order to achieve a most simple construction of the apparatus, it is beneficial to couple the piezoelectric elements to a common resonator, which extends substantially in the web running direction. This resonator is excited physically selectively by the individual piezoelectric elements, so that the ultrasonic pulses output exhibit very low divergence transversely with respect to the web running direction. In the web running direction, the divergence of the ultrasonic pulses output is considerably greater, so that the apparatus does not react to small disturbances such as frayed edges of the product web. The piezoelectric elements are preferably arranged in a row one behind another on the resonator and are separated by narrow gaps of less than 0.1 mm. In particular, consideration is given to forming the piezoelectric elements in one piece and connecting them to the resonator and only then separating them from one another by means of appropriate cuts. In this way, the result is a particularly low deviation of the resonant frequencies of the individual piezoelectric elements from one another, which simplifies their evaluation considerably.

In order to achieve focusing of the ultrasonic pulses by the reflector, it is beneficial if the reflector is curved concavely as viewed in the web running direction.

In order to achieve the most optimum focusing of the ultrasonic pulses, it is advantageous if the reflector has a center of curvature which lies in the region of the piezoelectric elements or of the resonator. The term "center of curvature" is in this case to be understood in a projection transversely with respect to the web running direction. In the case of a cylindrical design of the reflector, the centers of curvature lie on a common straight line which extends transversely with respect to the web running direction.

In particular if the ultrasonic pulses output diverge substantially only in the web running direction, it is not necessary to focus these transversely with respect to the web running direction. In this case, the reflector is preferably shaped cylindrically, so that it has a focusing action only in the web running direction. In this way, the result is the ability to produce the reflector particularly simply as a bent sheet metal part. In addition, the reflector can be configured without difficulty to be very long, so that it covers the entire region which the product web can occupy. It is therefore not necessary to configure the reflector to be displaceable in order to have it track the product web. Instead, it is sufficient to keep the reflector stationary. The reflector preferably has a circular or parabolic curvature in order to achieve an optimum focusing action.

Further advantages and features of the present invention will be presented in the following detailed description using the associated figures, which contain a plurality of exemplary embodiments of the present invention. However, it should be understood that the drawing is used only for the purpose of illustrating the invention and does not restrict the area of protection of the invention.

Figure 2:
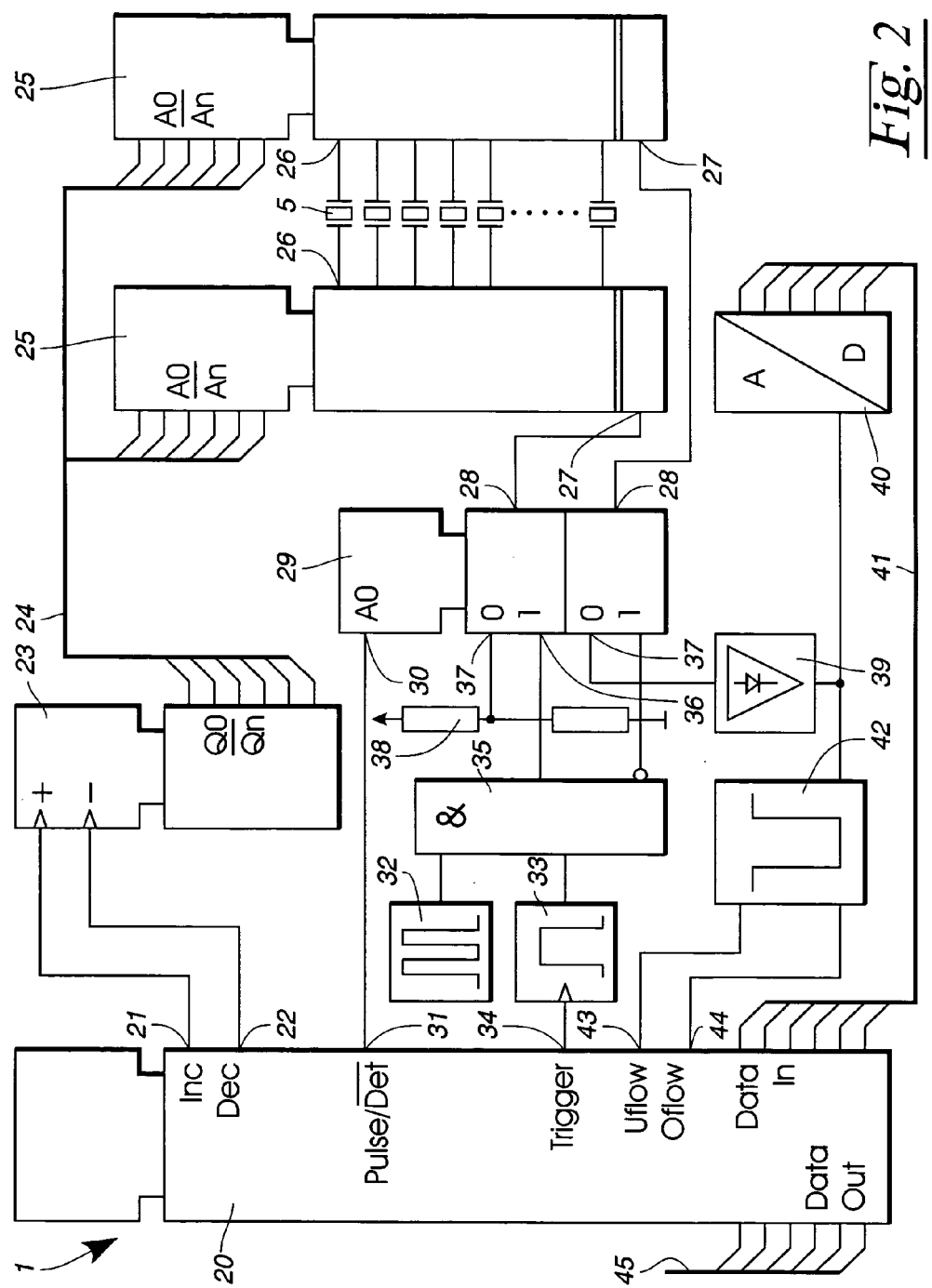

FIG. 1 shows a three-dimensional representation of an apparatus for detecting the edge position of a moving product web, and FIG. 2 shows a basic circuit diagram of the apparatus according to FIG. 1.

FIG. 1 shows the three-dimensional representation of an apparatus 1 for detecting an edge 2 of a moving product web 3. In this case, the product web 3 is moved in the direction 4, generally carrying out undesired movements transversely with respect to the web running direction 4. These undesired transverse movements lead to run-off of the product web 3 and are compensated for by appropriate product web guides which control the web run. In this case, the apparatus 1 is used as an actual value transmitter in order to determine the respective edge position.

The apparatus 1 for detecting the web edge 2 substantially comprises a number of piezoelectric elements 5 which are arranged beside one another and are fitted to a common resonator 6. The piezoelectric elements 5 are formed in one piece from a crystal, connected to the resonator and then separated from one another. Consideration is given in particular to soldering the piezoelectric elements 5 on to the resonator 6, vapor-deposited or sputtered electrodes being used as a soldering pad. Following the fitting of the piezoelectric elements 5, still connected in one place, to the resonator 6, these are separated from one another by cuts 7, so that they can oscillate independently of one another. In this way, the geometric dimensions of the individual piezoelectric elements 5 are identical within close tolerances, so that all the piezoelectric elements 5 have virtually the same resonant frequency.

The resonator 6 is preferably composed of a composite material, in particular glass fiber reinforced epoxy resin. On its surface 8, the resonator 6 is provided with a copper lamination 9, from which the necessary soldering areas and connecting leads for the operation of the piezoelectric elements 5 are etched free. In principle, consideration is also given to soldering the electronic components, in particular multiplexers and, if appropriate, preamplifiers, onto the resonator 6. In this way, the expenditure on cabling is reduced considerably, since only a very low number of leads have to be led to the resonator 6.

The piezoelectric elements 5 are used both as transmitters and as receivers and generate ultrasonic pulses 10 with a divergence in the web running direction 4 of between 10° and 60°. Transversely with respect to the web running direction 4, that is to say as viewed in the measuring direction of the apparatus 1, the divergence of the ultrasonic pulses 10 is less than 2° and therefore negligibly low. This difference in the divergences of the ultrasonic pulses 10 results from the geometric configuration of the resonator 6 with its longitudinal extent transverse with respect to the web direction 4, so that diffractions in this direction remain small.

Located opposite the piezoelectric elements 5 is a reflector 11, the product web 3 being provided between the piezoelectric elements 5 and the reflector 11. The reflector 11 reflects the incident ultrasonic pulses 10 back to the piezoelectric elements 5, said pulses in turn being converted by the latter into electrical signals. In order to achieve a high signal to noise ratio, the reflector 11, as viewed transversely with respect to the web running direction 4, is curved cylindrically, the centers of curvature 12 lying in the region of the resonator 6 of the piezoelectric elements 5. In this way, the ultrasonic pulses 10 are focused on to the resonator 6, so that the maximum possible sound energy is detected by the piezoelectric elements 5 and converted into an electrical signal. This high sound energy is particularly important to be able to suppress interfering signals, for example as a result of reflections on surrounding objects, effectively.

The product web 3 arranged between the piezoelectric elements 5 and the reflector 11 covers some of the piezoelectric elements 5, while the remainder of the piezoelectric elements 5 are free. The product web 3 is in this case formed such that it absorbs and/or reflects at least some of the ultrasonic pulses 10, so that, in the case of the piezoelectric elements 5 covered by the product web 3, only a fraction of the sound energy arrives as compared with the uncovered piezoelectric elements 5. This difference is used to determine the piezoelectric element 5 under which the product web edge 2 is located. Therefore, with little expenditure, a rough determination of the edge position of the product web 3 is provided.

In addition, in the case of that piezoelectric element 5 under which the product web edge 2 is located, the amplitude of the electrical signal generated by said piezoelectric element 5 is evaluated. From this evaluation, the level of coverage of the piezoelectric element 5 by the product web 3 can be determined directly. In particular, consideration is given, in order to convert the signal level into the corresponding edge position, to depositing appropriate calibration values in a computing unit, from which a calibration curve is interpolated. In this way, exact linearization of the transfer characteristic of the apparatus 1 is ensured.

FIG. 2 shows a schematic circuit diagram of the apparatus 1, the piezoelectric elements 5 being merely indicated by means of appropriate symbols. The apparatus 1 has a controller 20, which manages the entire time control of the circuit and the numerical processing of the measured data.

Via an increment output 21 and a decrement output 22, the controller 20 controls an up/down counter 23, whose counter reading determines the piezoelectric element 5 activated. The up/down counter 23 is connected via an address bus 24 to two analog multiplexers 25. These analog multiplexers 25 connect an output 26 corresponding to the address on the address bus 24 to an input 27 in each case. One of the piezoelectric elements 5 is in each case connected between the outputs 26 of equal weight. In this way, the two inputs 27 of the two analog multiplexers 25 are in each case connected to both electrodes of a selected piezoelectric element 5.

The two inputs 27 of the analog multiplexers 25 are connected to outputs 28 of a further analog multiplexer 29, which is formed as a 2 from 2 multiplexer. This analog multiplexer 29 has an address input 30 which is connected to a mode output 31 of the controller 20. This mode output 31 determines whether the piezoelectric elements 5 are operated as transmitters or receivers.

For the transmit operation, the apparatus 1 has an oscillator 32 which, if necessary, can also be clocked by the controller 20. Also provided is a monoflop 33, which is driven by a trigger output 34 of the controller 20. The oscillator 32 and the monoflop 33 are linked via an and gate 35, which generates a pulse train from the oscillations of the oscillator. This pulse train is supplied firstly inverted and secondly non-inverted to inputs 36 of the analog multiplexer 29. This measure achieves the situation where the piezoelectric elements 5 are operated at the full operating voltage, so that they output the greatest possible output signal.

In the receive mode, the piezoelectric elements 5 are connected to inputs 37 of the analog multiplexer 29. These inputs 37 are operatively connected firstly to a voltage divider 38 and secondly to a rectifying signal amplifier 39. The voltage divider 38 is used merely for setting a working point located within the operating voltage limits of the piezoelectric elements 5. The signal amplifier 39 amplifies the electrical signal generated by the piezoelectric elements 5 in order to make it accessible to further processing.

The signal amplifier 39 is operatively connected to an analog-digital converter 40, which transforms the amplified signal into a digital value. This digital value is supplied to the controller 20 via a data bus 41. In addition, the amplifier 39 is operatively connected to a window comparator 42, which compares the signal amplitudes with an upper and a lower limiting value. If the upper limit is exceeded or the signal falls below the lower limiting value, the window comparator 42 reports this to the controller 20 by means of active signals at its inputs 43 and 44, respectively.

The operation of the apparatus 1 will be explained in more detail in the following text. At the start of a measurement cycle, first of all, the product web edge 2 must be found roughly. This can be done, for example, by the controller initially emptying the counter 23 and then counting up successively via the increment output 21. Alternatively, consideration is also given to loading the counter 23 directly from the controller 20, in order to be able to use a faster algorithm, such as a successive approximation.

Following each selection of a new address on the address bus 24, a specific piezoelectric element 5 is selected by the analog multiplexer 25. The mode output 35 of the controller is then brought to logic 1 in order to connect the selected piezoelectric element 5 to the oscillator 32. By means of a trigger pulse on the trigger output 34, a pulse train from the oscillator 32 is generated, which acts on the selected piezoelectric element 5. This pulse train is converted in the piezoelectric element 5 into a mechanical movement which is output by the resonator 6.

As soon as the monoflop 33 returns to its inactive state again, the pulse train is terminated. After waiting for a specific dead time, determined by the controller 20, the mode output 31 is changed to logic 0 in order to operate the piezoelectric element 5 in the receive mode. At this time, it is connected to the signal amplifier 39, and the amplified and rectified signal is output to the controller 20 via the analog-digital converter 40 and the data bus 41. From the data arriving on the data bus 41, the controller 20 uses only that which arrives chronologically within approximately twice the signal propagation time between the piezoelectric element 5 and the reflector 11. The measured signal strength is converted by means of the calibration curve stored in the controller 20 into a coverage of the piezoelectric element 5 by the product web 3 and is output to a data bus 45. During this conversion, the counter reading of the counter 23, which determines which of the piezoelectric elements 5 was activated during the measurement, is additionally taken into account.

If the window comparator 42 reports an underflow or overflow of the signal strength on the input 43 or 44, this indicates that the product web edge 2 is no longer located under the selected piezoelectric element 5. Depending on whether an overflow or an underflow was indicated, the controller 20 supplies a pulse on its increment output 21 or its decrement output 22 in order for the counter 23 to count upward or downward. This procedure is repeated until the overflow or underflow is eliminated. Of course, it is also conceivable to implement the function of the window comparator 42 in the controller 20 by means of software, which evaluates the data arriving on the data bus 41 appropriately. In principle, all the components described can be implemented by the controller 20 in order to drive the piezoelectric elements 5.

Since some exemplary embodiments of the present invention are not shown or described, it is to be understood that a large number of changes and modifications of these exemplary embodiments described are possible without departing from the essential idea and the area of protection of the invention which is defined by the claims.

LIST OF DESIGNATIONS

1 Apparatus
2 Web edge
3 Product web
4 Web running direction
5 Piezoelectric element
6 Resonator
7 Cut
8 Surface
9 Copper lamination
10 Ultrasonic pulse
11 Reflector
12 Center of curvature
20 Controller
21 Increment output
22 Decrement output
23 Up/down counter
24 Address bus
25 Analog multiplexer
26 Output
27 Input
28 Output
29 Analog multiplexer
30 Address input
31 Mode output
32 Oscillator
33 Monoflop
34 Trigger output
35 And gate
36 Input
37 Input
38 Voltage divider
39 Signal amplifier
40 Analog-digital converter
41 Data bus
42 Window comparator
43 Input
44 Input
45 Data bus

The invention claimed is:

1. A method for detecting the position of an edge of a moving product web, in which piezoelectric elements situated on one side of the product web output ultrasonic pulses toward the product web, such that at least some of the ultrasonic pulses reach a reflector located on the other side of the product web and the ultrasonic pulses are reflected by the reflector back toward the piezoelectric elements, which receive the reflected ultrasonic pulses and convert them into electrical signals.

2. The method as claimed in claim 1, wherein the piezoelectric elements generate the ultrasonic pulses with a divergence which is greater in the web running direction than transversely with respect to the latter.

3. The method as claimed in claim 1, wherein the electrical signals from the piezoelectric elements are evaluated only after the expiry of a dead time following the output of the ultrasonic pulses for determining the edge position of the product web.

4. The method as claimed in claim 3, wherein the electrical signals from the piezoelectric elements are evaluated only within a time window, dependent on the distance of the reflector, for determining the edge position of the product web.

5. The method as claimed in claim 1, wherein the time difference between the output of the ultrasonic pulse and an electrical signal from the piezoelectric elements is registered, which signal is generated from a reflection of the ultrasonic pulse by the product web and the distance of the product web from the piezoelectric elements is determined from this time difference.

6. The method as claimed in claim 1, wherein the ultrasonic pulses are emitted simultaneously by a plurality of piezoelectric elements, only the electrical signal from one of these piezoelectric elements being evaluated.

7. The method as claimed in claim 1, wherein the reflector focuses the ultrasonic pulses, at least in the web running direction.

8. An apparatus for detecting the position of an edge of a moving product web, the apparatus comprising piezoelectric elements and a reflector located on opposite sides of the product web, said piezoelectric elements sending output ultrasonic pulses toward said reflector, said reflector reflecting the ultrasonic pulses back toward the piezoelectric elements, such that said piezoelectric elements receive the ultrasonic pulses reflected from said the reflector and convert them into electrical signal.

9. The apparatus as claimed in claim 8, wherein said piezoelectric elements are coupled to a common resonator, which extends substantially transversely with respect to the web running direction.

10. The apparatus as claimed in claim 8, wherein said reflector is curved concavely as viewed in the web running direction.

11. The apparatus as claimed in claim 10, wherein said reflector has a center of curvature which is located in the region of said piezoelectric elements.

12. The apparatus as claimed in claim 10, wherein said reflector has a center of curvature which is located in the region of the reflector.

13. The apparatus as claimed in claim 8, wherein said reflector is shaped cylindrically.

* * * * *

UNITED STATES PATENT AND TRADEMARK OFFICE
CERTIFICATE OF CORRECTION

PATENT NO.        : 7,151,715 B2
APPLICATION NO.   : 10/917911
DATED             : December 19, 2006
INVENTOR(S)       : Juergen Eisen, Wolfgang Krauth and Hans Seibold It is certified that error appears in the above-identified patent and that said Letters Patent is hereby corrected as shown below:

On the title page: Item [75] should read -- Hans Seibold --.

Signed and Sealed this

Thirteenth Day of March, 2007

JON W. DUDAS
*Director of the United States Patent and Trademark Office*